United States Patent [19]

Uekama et al.

[11] Patent Number: 4,869,904
[45] Date of Patent: Sep. 26, 1989

[54] SUSTAINED RELEASE DRUG PREPARATION

[75] Inventors: Kaneto Uekama, Kumamoto; Yoshiyuki Tahara, Tsurugashima; Takanori Ijitsu; Tadashi Yamada, both of Oi, all of Japan

[73] Assignee: Nisshin Flour Milling Co., Ltd., Tokyo, Japan

[21] Appl. No.: 127,699

[22] Filed: Dec. 2, 1987

[30] Foreign Application Priority Data

Dec. 26, 1986 [JP] Japan ................................. 61-308397

[51] Int. Cl.$^4$ ............................................. A61K 9/00
[52] U.S. Cl. ..................................... 424/400; 424/456; 424/470; 424/489; 424/502
[58] Field of Search ............... 424/468, 470, 489, 499, 424/456, 502

[56] References Cited

U.S. PATENT DOCUMENTS 4,695,467  9/1987  Uemura et al. ................ 424/489 X
4,722,815  2/1988  Shibanai .......................... 424/486 X

FOREIGN PATENT DOCUMENTS 59-084821  5/1984  Japan .................................. 424/499

Primary Examiner—Thurman K. Page
Attorney, Agent, or Firm—Larson and Taylor

[57] ABSTRACT

Now is provided a new sustained release drug preparation comprising such an inclusion complex of a medical compound with a hydrophobic cyclodextrin derivative, e.g. ethylated cyclodextrins, which sustains or retards the dissolution and release of the medical compound at a controlled rate from the inclusion complex and hence from the drug preparation containing the inclusion complex, so as to maintain the concentration of the medical compound in blood at an effective level for prolonged time. This drug preparation may further contain a second type of an inclusion complex of the medical compound with a hydrophilic cyclodextrin or hydrophilic cyclodextrin derivative, in mixture with the first type of the inclusion complex of the medical compound with a hydrophobic cyclodextrin derivative, to maintain the controlled release of the medical compound from the drug.

8 Claims, 6 Drawing Sheets

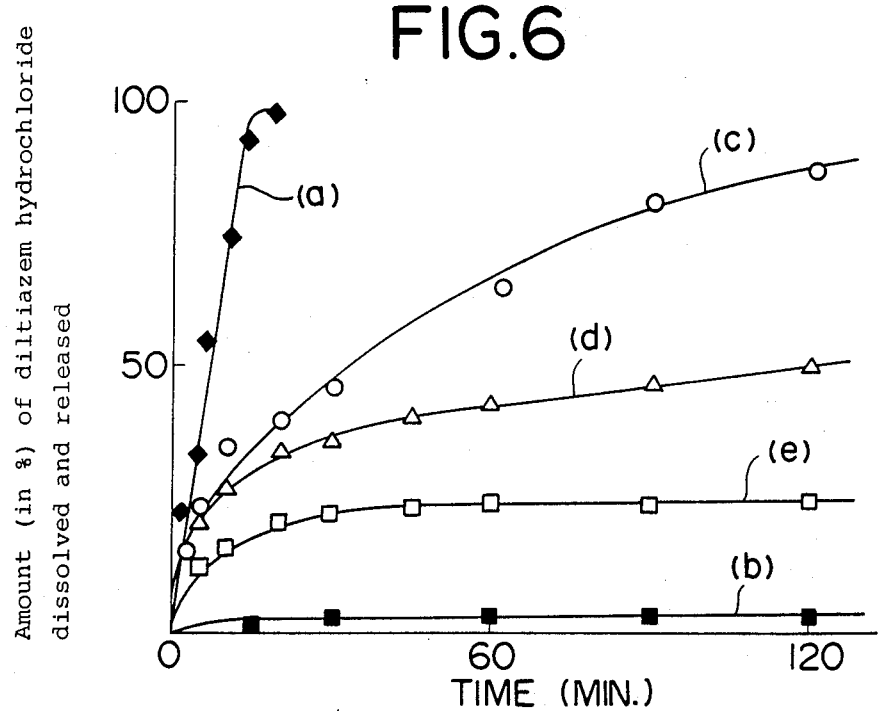

SUSTAINED RELEASE DRUG PREPARATION

SUMMARY OF THE INVENTION

This invention relates to a sustained release drug preparation, and more specifically to such a sustained release drug preparation, which comprises as the active ingredient an inclusion complex composed of at least one medical compound complexed with at least one hydrophobic cyclodextrin derivative, for example, one or more ethylated cyclodextrins.

Namely, this invention provides a medicinal preparation which comprises such a sustained release inclusion complex of at least one medical compound with at least one hydrophobic cyclodextrin derivative which permits the in vivo release rate of the medical compound from the inclusion complex and hence from the drug preparation to be lowered and controlled to maintain the blood concentration of the medical compound at an effective level for a longer period of time.

BACKGROUND OF THE INVENTION

A variety of measures has conventionally been practised with respect to sustained release drug preparations, namely, with respect to such drug preparations containing a medical compound and capable of retarding or prolonging the release of the medical compound from the drug preparation to maintain the efficacy of the medical compound in vivo for a long time. For example, there have been practised such method where crystals, granules or tablets comprising medical compound are coated with a hydrophobic substance such as wax or the like; such method where a large amount of a binder and/or a hydrophobic lubricant is or are mixed with medical compound; and such method where a medical substance is wrapped with a semipermeable membrane. On the other hand, it is known that inclusion complex may be obtained by complexing a guest compound or molecule with cyclodextrin as a host compound or molecule. And, such inclusion complexes with cyclodextrin have been used almost for the purpose of enhancing the stability of a guest compound against heat or light or in air (Japanese Patent Application first publication "Kokai" No. 154479/81), for the purpose of masking a bitter taste or unpleasant odor of a guest compound (Japanese Patent Application first publication "Kokai" No. 137867/81), for the purpose of solubilizing a hardly soluble substance (Japanese Patent Application first publication "Kokai" No. 48849/81), for the purpose of utilizing as emulsion stabilizers (Japanese Patent Application first publication "Kokai" No. 21552/81), or for the purpose of improving absorption rate of a guest compound in vivo. But, no attempt has heretofore been made that such an inclusion complex, which is obtained by complexing a guest compound with cyclodextrin as a host compound, is used with a view to achieving sustained release of or prolonged maintenance of the medical efficacy of a medical compound.

We, the present inventors, have carried out extensive investigations on the possibility that such inclusion complexes, which are formed by complexing cyclodextrin or cyclodextrin derivative as a host compound with a guest compound which is a medical compound capable of acting as an active ingredient in a drug, would be used as a drug or in the form of a sustained release drug preparation. As a result, we have now found that when medical compound is used as the guest compound and complexed with a hydrophobic alkylated cyclodextrin derivative as a host compound for formation of their inclusion complexes, such hydrophobic alkylated cyclodextrin derivatives, for example, ethylated cyclodextrin derivatives can have significant effects for the retardation of release of medical compound from said inclusion complexes, whereas hydrophilic $\alpha$-, $\beta$-and $\gamma$-cyclodextrins and the other, hydrophilic cyclodextrin derivatives such as methylated cyclodextrin, hydroxypropylated cyclodextrin and branched cyclodextrin, which have conventionally been used as the host compound of the known inclusion complexes, do not have any substantial sustaining effects on the release of medical compound. Thus, we have found that formation of an inclusion complex by complexing a medical compound with a hydrophobic alkylated cyclodextrin can achieve so-called "molecular level" encapsulation of the medical compound, and hence that it is possible to develop such a sustained release inclusion complex and also such a sustained release drug preparation comprising said inclusion complex, which permit sustained and gradual release of the medical compound in vivo. On the basis of these findings, we have accomplished this invention. Incidentally, parts of the above finding were reported by the present inventors and certain associates at page 18 of a literature "Ko-en Yo-shi Shu of Fifth Cyclodextrin Symposium" published on 5 Dec. 1986 in Kyoto, Japan.

The previous procedures for retardation of release of a medical compound by coating or encapsulating the medical compound with some materials in an attempt to provide a sustained release drug preparation were tried but were not always satisfactory because of the difficulties involved in the selection of a coating agent or encapsulating material, the complexity of the coating or encapsulation procedures and the difficulties in the control of reproducibility of release retarding effects. In these circumstances, we, the present inventors, already tried to prepare and utilize such an inclusion complex where a hydrophilic cyclodextrin derivative was used as a host compound, and we conducted some research accordingly. Our previous research, however, failed to develop any drug preparation having significant release retarding effects.

Thereafter, in an attempt to provide the sustained release drug preparations, we have continued our researches with using as the host compounds such various cyclodextrin derivatives which are either hydrophobic or poorly soluble in water and which can form an inclusion complex with medical compound. As a result, we have now found that a hydrophobic alkylated cyclodextrin derivative, for example, ethylated cyclodextrins is suitable as the host compound to be complexed with a medical compound for formation of their inclusion complex, and is suitable for the production of sustained release drug preparations.

We have further found that, with an inclusion complex of a medical compound with a hydrophobic cyclodextrin derivative, the inherent medical activities of the medical compound can be maintained in vivo for a prolonged duration without modifying its inherent effectiveness. Moreover, the drug preparation comprising the above inclusion complex may take any dosage form. We have also found that the drug preparation comprising the inclusion complex according to the present invention may be either in the form of liquid preparation forms, such as injections and suspensions, or in the form of solid preparation forms such as tablets, powder, granules and capsules. According to the present invention, the designing of a drug preparation and maintenance of its quality can also be facilitated, since the sustained release of a medical compound from said complex is retained independently of pH. It is also expected that an inclusion complex of medical compound with a hydrophobic cyclodextrin derivative involks some changes in the physiochemical properties of the medical compound, whereby the stability of the medical compound against light and/or heat may be improved.

Thus, we, the present inventors, have found that when a medical compound has been complexed with a hydrophobic cyclodextrin derivative, for example, ethylated cyclodextrins to form their inclusion complex, the release of the medical compound from said complex can be controlled to less than the rate of dissolution and release of the medical compound itself. Furthermore, we have found that the hydrophobic ethylated cyclodextrin derivatives available according to this invention include the three particular compounds, namely heptakis(2,3-di-O-ethyl)-β-cyclodextrin; heptakis(2,6-di-O-ethyl)-β-cyclodextrin; and heptakis(2,3,6-tri-O-ethyl)-β-cyclodextrin, and that these three particular ethylated β-cyclodextrin derivatives can show different effects of sustaining the release of the medical compound from the inclusion complex. Thus, the release of a medical compound from the inclusion complex may be adjusted to a desired extent by selecting well these three particular ethylated β-cyclodextrin derivatives suitably in combination for use in the formation of the inclusion complexes.

DETAILED DESCRIPTION OF THE INVENTION

In one aspect of this invention, a medical compound is complexed with a hydrophobic cyclodextrin derivative to form an inclusion complex, and the sustained release property in vivo of the medical compound from the resultant inclusion complex as formed is utilized in a sustained release drug preparation.

According to this invention, therefore, there is provided a sustained release drug preparation, which comprises an inclusion complex composed of at least one medical compound complexed with at least one hydrophobic cyclodextrin derivative, as the active ingredient, without or in association with a pharmaceutically acceptable carrier or vehicle for said inclusion complex.

Here, by the term "an inclusion complex composed of at least one medical compound complexed with at least one hydrophobic cyclodextrin derivative" is referred briefly to as "inclusion complex of medical compound with hydrophobic cyclodextrin derivative", for sake of simplicity. The cyclodextrin compounds are cyclic compounds having the cylindric molecular structure, of which the inner surface and the outer surface are different in their hydrophilic or lipophilic nature, permitting other molecules, known as "guest molecules" of suitable dimensions, or parts thereof, to penetrate into the intramolecular cavity of the inner part of the cylindric cyclodextrin "host molecule", thereby forming the inclusion complex.

The hydrophobic cyclodextrin derivatives useful in this invention may include an alkylated cyclodextrin which has been substituted by an alkyl group higher than methyl group. It should also be borne in mind that a mixed methylated/alkylated cyclodextrin, which may be obtained by substituting some of the methyl groups of a methylated cyclodextrin with higher alkyl groups such as ethyl groups, for example, a mixed methylated/ethylated cyclodextrin is also embraced by the term "alkylated cyclodextrin" as used herein.

An alkylated cyclodextrin, which is usable preferably in the present invention, includes ethylated cyclodextrins, as will be described subsequently. The other alkylated cyclodextrins of which alkyl substituents are each an alkyl group higher than the ethyl group, for example, propylated cyclodextrin, butylated cyclodextrin and the like may also be used.

In the sustained release drug preparation of the present invention, it is also possible that the above-described inclusion complex of a medical compound with a hydrophobic cyclodextrin derivative is used in mixture with a second type of another inclusion complex of a medical compound with a hydrophilic natural cyclodextrin or a hydrophilic cyclodextrin derivative, for example, methylcyclodextrin. In this case, the release of the medical compound from the drug may be controlled to a desired extent by adjusting appropriately the mixing ratio of the above two types of inclusion complexes. For the method of preparing the above mixture of the abovementioned first and second two types of inclusion complexes, it is possible to use such a method where the medical compound is complexed directly with a mixture of a hydrophobic cyclodextrin derivative with a hydrophilic natural cyclodextrin or a hydrophilic cyclodextrin derivative, or such a method where the abovementioned two types of inclusion complexes each are produced separately and then mixed together at a suitable mixing ratio. As specific examples of the above-described hydrophilic natural cyclodextrin and hydrophilic cyclodextrin derivative, may be mentioned α-, β- and γ-cyclodextrins, as well as methylated cyclodextrin, hydroxypropylated cyclodextrin and branched cyclodextrins, for example, martosyl cyclodextrin, glucosyl cyclodextrin, and the like.

The medical compound useful for the formation of the inclusion complex in this invention is generally called "guest compound or molecule". No particular limitation is imposed on the nature of medical compound. All kinds of medical compounds which are capable of forming the inclusion complexes with a hydrophobic cyclodextrin may be used here, so that the resultant inclusion complexes show the sustained release property of medical compound. Hydrophilic, medical compounds are particularly preferred. The hydrophobic cyclodextrin derivative can easily form the inclusion complexes especially when such medical compounds are in the form of their acid addition salts such as hydrochlorides, nitrates, sulfates or organic acid salts.

The kinds, i.e., the range of medical compounds, which are usable for the formation of inclusion complex in the present invention, includes all medical compounds, of which the release from the complex can be retarded or sustained when inclusion-complexed with a hydrophobic cyclodextrin derivative. As illustrative examples of such medical compounds, may be mentioned analgesic drugs, antipyretic drugs, antiarrhythmic drugs, vitamins, antiinflammatory drugs, coronary vasodilators, venous vasodilators, bronchodilators, antiinfection drugs, psychotropics, antihistammics, muscle relaxants, antidiarrheal drugs, aperitives, anorectics, antihypertensive drugs, antibiotics, tranquillizers, antitumor agents, sedative drugs, antiemetics, antispsmodics, antihypoglycemics and antihyperglycemics, diuretics, antitussives, sputum removers, anti-asthematic drugs, alternatives, antirheumatics, etc.

These medical compounds may each be used, so long as they form the inclusion complexes with a hydrophobic cyclodextrin derivative in accordance with the present invention. As specific examples of the medical compound usable as the guest molecule for formation of the inclusion complex with a hydrophobic cyclodextrin derivative, may be mentioned cardiac vasodilators such as diltiazem hydrochloride, isosorbid nitrate, 1,4-dihyropyridine derivatives, papaverine hydrochloride, isoporterenol hydrochloride and verapamil hydrochloride as well as vasodilators such as ifenprodil tartrate and dilazep hydrochloride. These medical compounds can form the inclusion complexes with the hydrophobic cyclodextrin derivative, which may be formulated into sustained release drug preparations.

The inclusion complex which may be used according to this invention is a complex composed of a medical compound as the guest molecule complexed with a hydrophobic cyclodextrin derivative, preferably, an alkylated cyclodextrin as the host molecule. The molar ratio of the guest molecule to the host molecule may generally be in a range of from 1:1 to 1:10 for the attainment of the objects of this invention, with the molar ratio of 1:1–1:3 being preferable from the practical viewpoint.

Of the cyclodextrins, such those which are composed of 6, 7 and 8 molecules of D-glucopyranose, the structural unit of the cyclodextrin, as coupled together in the cyclic structure, are generally called $\alpha$-, $\beta$- and $\gamma$-cyclodextrins, respectively. They are "natural" cyclodextrins of the hydrophilic nature, but the release-sustaining effects cannot be observed with the inclusion complexes of medical compound with such "natural" cyclodextrins.

The ethylated cyclodextrins, specific examples of alkylated cyclodextrins useful in the practice of this invention, will next be described in further detail.

The ethylated cyclodextrins are known compounds and include three types of such modified dextrins which may be obtained respectively by chemically substituting ethoxy groups for the two hydroxyl groups at the 2- and 3-positions, the two hydroxyl groups at the 2- and 6-positions, and the three hydroxyl groups at the 2-, 3- and 6-positions of the D-glucopyranose units, the structural unit of $\beta$-cyclodextrin, and which are specifically the aforesaid heptakis(2,3-di-O-ethyl)-62 -cyclodextrin (hereinafter called "2,3-DE-$\beta$-CyD"), heptakis (2,6-di-O-ethyl)-$\beta$-cyclodextrin (hereinafter called "2,6-DE-$\beta$-CyD"), and heptakis(2,3,6-tri-O-ethyl)-$\beta$-cyclodextrin (hereinafter called "2,3,6-TE-$\beta$-CyD"). The molecular weights of these individual ethylated cyclodextrins are 1527 for the diethyl derivatives and 1723 for the triethyl derivative. They are each soluble easily in organic solvents but poorly soluble in water, and have a low hygroscopicity and a high surface activity. Differences in the sustained release property are observed among the respective inclusion complexes of medical compound with these three types of the ethylated cyclodextrins. Namely, their release sustaining effect on medical compound (their ability to control the release rate of medical compound) increases in the order of 2,3-DE-$\beta$-CyD, 2,6-DE-$\beta$-CyD and 2,3,6-TE-$\beta$-CyD.

In another aspect of this invention, there is also provided a method for complexing a medical compound with a hydrophobic cyclodextrin derivative.

The complexing method according to this invention may be carried out by the kneading method, solution method, lyophilizing method or the like, which has been known in the art for production of inclusion complexes.

An illustrative process of producing an inclusion complex according to this invention, with making use of the kneading method, for example, will hereinafter be described.

In order to produce the inclusion complex in accordance with this invention by the kneading method, it is suitable that the molar ratio of the guest molecule to the host molecule may generally range from 1:1 to 1:10, with a ratio of 1:1–1:3 being preferred. The molar ratio of 1:1 is still practical sufficiently. A powder of a medical compound and a powder of a hydrophobic cyclodextrin derivative are taken by weighing, and they may be mixed together to prepare a mixture of them at a suitable molar ratio. To this powdery mixture is added purified water in such an amount that makes the resulting aqueous mixture to resemble a sol. The aqueous mixture is thereafter kneaded sufficiently until the mixture is converted into a paste-like state. The mixture is then dried by evaporation of water under reduced pressure or by other method, thereby obtaining an inclusion complex of medical compound with hydrophobic cyclodextrin derivative, in the form of powder. Although no particular limitation is imposed on the kneading temperature, it is preferred that the kneading is carried out in a cold and dark room, as needed. However, the mixing and kneading may be conducted usually at room temperature under diffuse light. A duration of 0.5–2 hours is sufficient as the kneading time, although it varies dependent on the amount of a complex sample to be produced. An inclusion complex as obtained by the above-described kneading method may then be purified, whenever needed.

In this invention, the production of the inclusion complex can be achieved by any known complexing method as described above. As exemplary solvents useful for these complexing procedures, may be mentioned water, acetone, methanol, ethanol, dioxane, tetrahydrofuran, ethyl methyl ketone, n-propanol, isopropanol, isobutyl methyl ketone, acetonitrile, isobutanol, diethyl ether, dichloromethane, chloroform, toluene, etc. It is feasible to use a mixture of two or more of these exemplified solvents. Among these solvents, water, acetone, ethanol, dioxane, tetrahydrofuran, dichloromethane and toluene can be used most preferably.

The formation of an inclusion complex of a medical compound with an alkylated cyclodextrin derivative in accordance with the process described above was confirmed by various methods such as powder X-ray diffraction, dissolution behavior, scanning electron microscope analysis, differential thermal analysis (DTA) and infrared absorption (IR). Inclusion complexes were prepared using diltiazem hydrochloride as an exemplary medical compound, and the behavior of dissolution and release of diltiazem from the inclusion complex in the powder form, as well as the behavior of dissolution and release of diltiazem from compressed tablets containing the inclusion complex were determined in order to confirm the complexing reaction and to evaluate the sustained release property, respectively. Further, the inclusion complex was administered orally to rats, and changes in the plasma concentration of the medical compound were then measured. While taking the determined dissolution and release behavior of the diltiazem into parallel consideration, the achievement of the sustained release property of the inclusion complex was confirmed. It was also proven that the dissolution and release rate of the medical compound, diltiazem, could be controlled at will, by using the ethylated cyclodextrins as the host compound for formation of inclusion complexes. Details of inclusion complex of diltiazem hydrochloride with an ethylated cyclodextrin (molar ratio: 1:1) will hereinafter be described.

Powder X-ray diffraction patterns of inclusion complexes of diltiazem hydrochloride with an ethylated cyclodextrin are shown in FIG. 1. More particularly, in FIG. 1, there are shown the powder X-ray diffraction pattern of diltiazem hydrochloride itself (Curve A); that of 2,6-DE-$\beta$-CyD (Curve B); that of an inclusion complex of diltiazem hydrochloride with 2,6-DE-$\beta$-CyD at molar ratio of 1:1 (Curve C); that of diltiazem hydrochloride itself (Curve D); that of 2,3,6-TE-$\beta$-CyD (Curve E); and that of an inclusion complex of diltiazem hydrochloride with 2,3,6-TE-$\beta$-CyD at molar ratio of 1:1 (Curve F). With the X-ray-diffraction patterns of these inclusion complexes of diltiazem hydrochloride with an ethylated cyclodextrin, the characteristic peaks of the individual components have disappeared, but instead, such a diffraction pattern which is different from the diffraction patterns of a physical mixture of both the components has been given. These results of the X-ray diffraction patterns support the fact that diltiazem hydrochloride and an ethylated cyclodextrin have complexed with each other and formed an inclusion complex of them having a structure different from the original crystalline structures of the individual components.

FIG. 2 illustrates the dissolution behavior of diltiazem hydrochloride alone, the dissolution behavior of a physical mixture of diltiazem hydrochloride with ethylated cyclodextrin at a molar ratio of 1:1, and the dissolution behavior of inclusion complexes of diltiazem hydrochloride with ethylated cyclodextrin at molar ratio of 1:1, when each sample in the powder form was dissolved in water. More particularly, in FIG. 2, there are shown a curve which exhibits a variation with time in the amount (in %) of a powdery diltiazem hydrochloride alone as dissolved and released in water when the powder was placed into water (Curve a); a curve which exhibits a variation with time in the amount (in %) of diltiazem hydrochloride as dissolved and released from a powdery inclusion complex of diltiazem hydrochloride with 2,3-DE-$\beta$-CyD at molar ratio of 1:1 when this powdery complex was placed into water (Curve b); a curve which exhibits a similar variation in the amount (in %) of diltiazem hydrochloride as dissolved and released from a powdery inclusion complex of diltiazem hydrochloride with 2,6-DE-$\beta$-CyD at molar ratio of 1:1 (Curve c); a curve which exhibits a similar variation in respect of a physical mixture of diltiazem hydrochloride with 2,6-DE-$\beta$-CyD at molar ratio of 1:1 (Curve d); and a curve which exhibits a similar variation in respect of a powdery inclusion complex of diltiazem hydrochloride with 2,3,6-TE-$\beta$-CyD at molar ratio of 1:1 (Curve e).

From the curves of FIG. 2, it is seen that diltiazem hydrochloride itself was dissolved in water to an extent of 100% in about 5 minutes when tested by dissolving it alone, whereas the retarded release of the medical compound was involved in the case of the inclusion complexes of the diltiazem with an ethylated cyclodextrin. The release retarding effects, which are obtained by complexing diltiazem hydrochloride with an ethylated cyclodextrin, increased in the order of 2,3-DE-$\beta$-CyD < 2,6-DE-$\beta$-CyD < 2,3,6-TE-$\beta$-CyD.

Further, a physical mixture of diltiazem hydrochloride with lactose, and a physical mixture of diltiazem hydrochloride with starch were prepared at molar ratio of 1:1 and compressed to form tablets, respectively. Inclusion complexes of diltiazem hydrochloride with an ethylated cyclodextrin, more particularly an inclusion complex of diltiazem hydrochloride with 2,6-DE-$\beta$-CyD at molar ratio of 1:1; and an inclusion complex of diltiazem hydrochloride with 2,3,6-TE-$\beta$-CyD at molar ratio of 1:1 were also compressed to form tablets, respectively. These tablet samples were each placed in Japanese Pharmacopoeia First Fluid (pH 1.2) or Japanese Pharmacopoeia Second Fluid (pH 6.8) to observe the behaviors of dissolution and release of the diltiazem hydrochloride from these tablets into these fluids. The dissolution and release behavior into the First Fluid is shown in FIG. 3, and that into the Second Fluid is shown in FIG. 4.

More particularly, in FIG. 3, there are shown a curve which exhibits a variation with time in the amount (in %) of diltiazem hydrochloride (abbreviated as DH hereinafter) as dissolved and released from the tablet of the physical mixture of DH and lactose when this mixture was placed in the First Fluid (Curve a); a curve which exhibits a similar variation in respect of the tablet of the physical mixture of DH and starch (Curve b); a curve which exhibits a similar variation in respect of the tablet of the inclusion complex of DH with 2,6-DE-$\beta$-CyD (Curve c); and a curve which exhibits a similar variation in respect of the tablet of the inclusion complex of DH with 2,3,6-TE-$\beta$-CyD (Curve d). In FIG. 4, there are shown the curves which are corresponding to the curves of FIG. 3 respectively when the respective tablet samples were separately placed in the Second Fluid. From the results as shown in FIGS. 3 and 4, it is observed that in the case of the tablets containing starch or lactose as the excipient, these tablets were disintegrated and dissolved completely in 5-10 minutes. In contrast, the tablets of the DH-ethylated cyclodextrin-inclusion complexes were able to significantly retard the dissolution and release of the medical compound (DH) from the respective tablets in the order of 2,6-DE-$\beta$-CyD < 2,3,6-TE-$\beta$-CyD. Similar release retarding effects were also observed when tested in the Japanese Pharmacopoeia Second Fluid. Normally, a medical compound itself has pH-dependency for its dissolution, and it is usual that a medical compound is much soluble in an aqueous medium of higher acidity. In ordinary designing of a drug preparation, it is necessary to employ such a formulation that an enteric coating or the like is applied on the medical compound to avoid its dissolution in the stomach juice. No pH dependency was, however, observed on the medical compound which has been complexed into an inclusion complex with an ethylated cyclodextrin, so that the enteric formulation is then not required for the inclusion complex of this invention. In other words, the above observations indicate that a "pH-independent" powder or solution formulation may be obtained even using a "pH-dependent" medical compound, as far as such medical compound has been complexed with an ethylated cyclodextrin to form their inclusion complex.

FIG. 5 illustrates curves which exhibit variations with time in the plasma concentrations of diltiazem as measured by high-performance liquid chromatography (HPLC) after oral administration to rats of such tablets which were prepared by compressing a physical mixture of diltiazem hydrochloride with starch, or the inclusion complexes of diltiazem hydrochloride with an ethylated cyclodextrin. More particularly, in FIG. 5, there are shown a curve which exhibits a variation with time in the plasma concentration (ng/ml) of diltiazem in rats as measured by high-performance liquid chromatography (HPLC) when such tablets as prepared by compression of a physical mixture of diltiazem hydrochloride (abbreviated as DH) with starch at molar ratio of 1:1 were administered orally to the rats (Curve a); a curve which exhibits a variation with time in the plasma concentration (ng/ml) of diltiazem in rats as measured by HPLC when such tablets as prepared by compression of an inclusion complex of DH with 2,6-DE-$\beta$-CyD at molar ratio of 1:1 were given orally to the rats (Curve b); and a curve which exhibits a similar variation in the plasma concentration (ng/ml) of diltiazem when such tablets as prepared by compression of an inclusion complex of DH with 2,3,6-TE-$\beta$-CyD at molar ratio of 1:1 were orally given to the rats (Curve c). By mutual comparison of these curves of FIG. 5, it is observed that the diltiazem was absorbed promptly into the blood and disappeared quickly from the blood when the physical mixture of DH with starch in the compressed tablet form was orally given, and that in contrast, diltiazem was maintained in the blood at substantially steady concentrations for prolonged period of time when the inclusion complexes of DH with an ethylated cyclodextrin in the compressed tablet form were orally given, as will be seen from the patterns of the curves in FIG. 5. Furthermore, pharmacokinetic parameters which were obtained in the above tests are tabulated in Table 1 below. It will be appreciated from these parameters of Table 1 that the time ($T_{max}$) as required to reach the maximum plasma concentration ($C_{max}$) of diltiazem; and the mean residence time (MRT) of diltiazem have been prolonged substantially with the administration of the inclusion complex of diltiazem hydrochloride with ethylated cyclodextrin. Besides, AUC (namely, Area under the plasma concentration-time curve) of diltiazem was evaluated from the Curves a, b and c of FIG. 5, and the determined values of AUC are tabulated in Table 1 below in respect of the respective tablet samples as tested.

TABLE 1

| Tested tablet samples | $C_{max}$ (ng/ml) | $T_{max}$ (min.) | AUC* (hours · ng/ml) | MRT (hours) |
| --- | --- | --- | --- | --- |
| Physical mixture of diltiazem.HCl and starch | 200 | 15 | 300 | 4.0 |
| Inclusion complex of diltiazem.HCl with 2,6-DE-$\beta$-CyD | 80 | 80 | 810 | 7.5 |
| Inclusion complex of diltiazem.HCl with 2,3,6-TE-$\beta$-CyD | 20 | 45 | 140 | 7.3 |

*AUC: Area under the plasma concentration-time curve.

In the foregoing, it is described that the release of a medical compound from the drug preparation can be controlled to a desired extent by adjusting the mixing ratio at which (i) the first type of an inclusion complex of medical compound with a hydrophobic cyclodextrin derivative such as ethylated cyclodextrin is mixed with (ii) the second type of an inclusion complex of medical compound with a hydrophilic natural cyclodextrin or a hydrophilic cyclodextrin derivative to prepare a mixture of these first and second two types of the inclusion complexes. When this mixture of these two types of the inclusion complexes is used and formulated into a drug preparation with or without suitable excipient, the dissolution and release of the medical compound from the drug preparation can be adjusted to a controlled rate by changing appropriately the mixing ratio of the first type of the inclusion complex to the second type of the inclusion complex in a range of 1:2 to 1:0.1 by weight, preferably in a range of 1:2 to 1:0.25 by weight, more specifically in a range of 1:2 to 1:0.3. In general, the rate of dissolution and release of the medical compound from such a drug preparation comprising the above-mentioned two types of the inclusion complexes can be increased more than that from such a drug preparation comprising exclusively the first type of the inclusion complex, namely the inclusion complex of medical compound with a hydrophobic cyclodextrin derivative.

In further aspect of this invention, therefore, there is provided a sustained release drug preparation, which comprises (i) an inclusion complex of a medical compound with a hydrophobic cyclodextrin derivative and (ii) an inclusion complex of a medical compound with a hydrophilic cyclodextrin or a hydrophilic cyclodextrin derivative, as a mixture of the complex (i) and the complex (ii) at a mixing ratio of 1:2 to 1:0.1 by weight, as the active ingredient, without or in association with a pharmaceutically acceptable vehicle or excipient.

According to particular embodiment of this invention, there is provided a sustained released pharmaceutical composition in the form of compressed tablets or granules, which comprises (i) an inclusion complex of diltiazem or its acid addition salt, isosorbide or its acid addition salt or dicardipin or its acid addition salt with a hydrophobic cyclodextrin derivative at a molar ratio of the medical compound to the cyclodextrin derivative of 1:1 to 1:10, plus (ii) an inclusion complex of a medical compound as specified above with a hydrophilic cyclodextrin or a hydrophilic cyclodextrin derivative at a molar ratio of 1:1 to 1:10, as the active ingredient, and which is in the form of a physical mixture of the inclusion complex (i) with the inclusion complex (ii) at a mixing ratio of 1:2 to 1:0.1, preferably of 1:2 to 1:0.25 by weight.

Now, to demonstrate the behaviors of dissolution and release of the medical compound from the sustained release pharmaceutical composition according to this particular embodiment of this invention, the following tests were conducted. Thus, an inclusion complex of diltiazem hydrochloride (DH) with 2,3,6-TE-$\beta$-CyD which shows a highly controlled release rate of DH therefrom was mixed at varying ratios with an inclusion complex of DH with hydrophilic $\beta$-cyclodextrin ($\beta$-CyD) which can fastly release DH therefrom, and the resulting mixtures were separately compressed directly (without addition of vehicle or excipient) to form the respective tablet samples. The respective tablet samples were separately placed into water and the amount (in %) of DH as dissolved and released into water from the tablet was determined with lapse of time, to plot the curves which show the variation with time in the amount (in %) of DH as dissolved from each sample. The behaviors of dissolution of DH as depicted by the curves plotted as above are shown in FIG. 6. More particularly, in FIG. 6, there are shown a curve which exhibits a variation with time in the amount (in %) of DH as dissolved and released when a tablet-shaped inclusion complex of DH with hydrophilic $\beta$-CyD (at molar ratio of 1:1) as a comparative sample was placed into water (Curve a); a curve which exhibits a similar variation in the amount (in %) of DH as dissolved and released from the tablet-shaped inclusion complex of DH with 2,3,6-TE-$\beta$-CyD (at molar ratio of 1:1) when placed in water (Curve b); a curve which exhibits a similar variation in the amount (in %) of DH as dissolved and released from a tablet-shaped mixture (at ratio of 1:1 by weight) of an inclusion complex of DH with $\beta$-CyD (at molar ratio of 1:1) plus an inclusion complex of DH with 2,3,6-TE-$\beta$-CyD (at molar ratio of 1:1) when placed in water (Curve c); a curve which exhibits a similar variation in the amount (in %) of DH as dissolved and released from a tablet-shaped mixture (at ratio of 3:7 by weight) of an inclusion complex of DH with $\beta$-CyD (at molar ratio of 1:1) plus an inclusion complex of DH with 2,3,6-TE-$\beta$-CyD (at molar ratio of 1:1) when placed in water (Curve d); and a curve which exhibits a similar variation in the amount (in %) of DH as dissolved and released from a tablet-shaped mixture (at ratio of 2:8 by weight) of an inclusion complex of DH with $\beta$-CyD (at molar ratio of 1:1) plus an inclusion complex of DH with 2,3,6-TE-$\beta$-CyD (at molar ratio of 1:1) when placed in water (Curve e).

From mutual comparisons of the curves of FIG. 6, it is revealed that the rate of release of medical compound from the tablets made by compression of the mixture of the diltiazem HCl-$\beta$-CyD inclusion complex and the diltiazem HCl-ethylated-$\beta$-CyD inclusion complex can be adjusted to a controlled rate when such inclusion complex with the hydrophobic ethylated cyclodextrin derivative which permits the release of medical compound at a low rate and such inclusion complex with the hydrophilic $\beta$-cyclodextrin which permits the release of medical compound at a high rate are used at a suitably selected mixing ratio by weight to form their mixture of the abovementioned two types of the inclusion complexes.

With reference to the accompanying Drawings and in brief:

Figure 1:
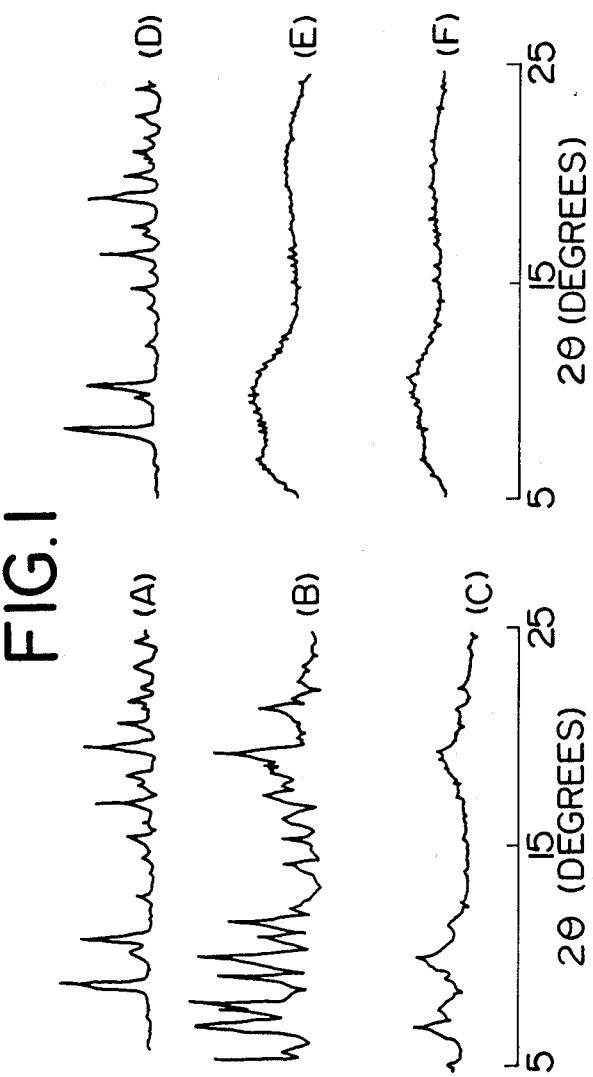
FIG. 1 shows X-ray diffraction patterns of diltiazem HCl; some exemplary ethylated $\beta$-cyclodextrins; and some exemplary inclusion complexes according to this invention.
Figure 2:
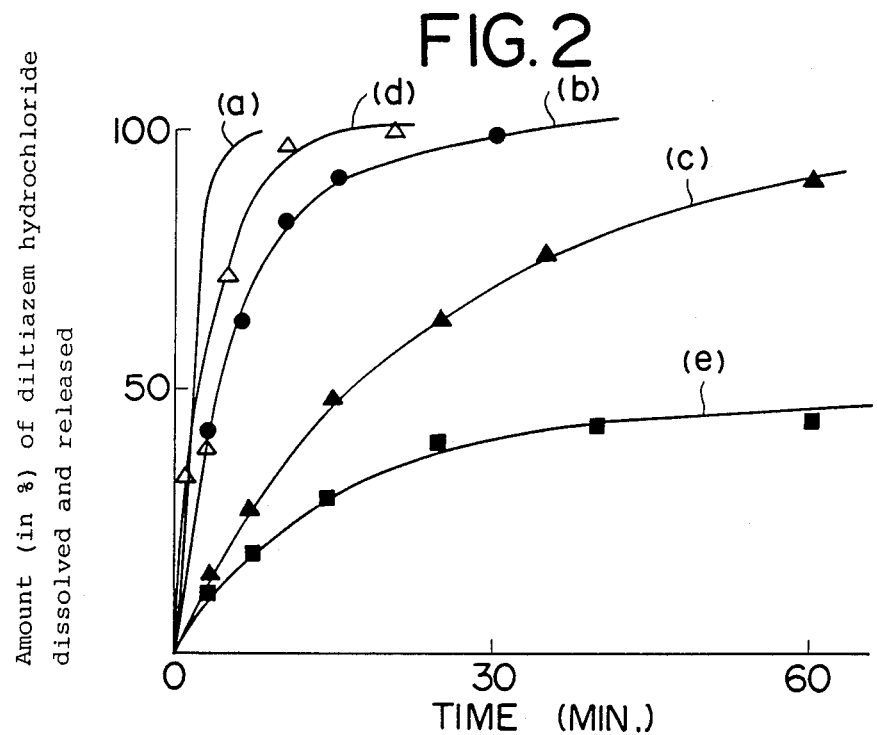
FIG. 2 illustrates the behaviors of dissolution and release of diltiazem HCl; and some exemplary inclusion complexes according to this invention, together with that of a physical mixture of the component substances.
Figure 3:
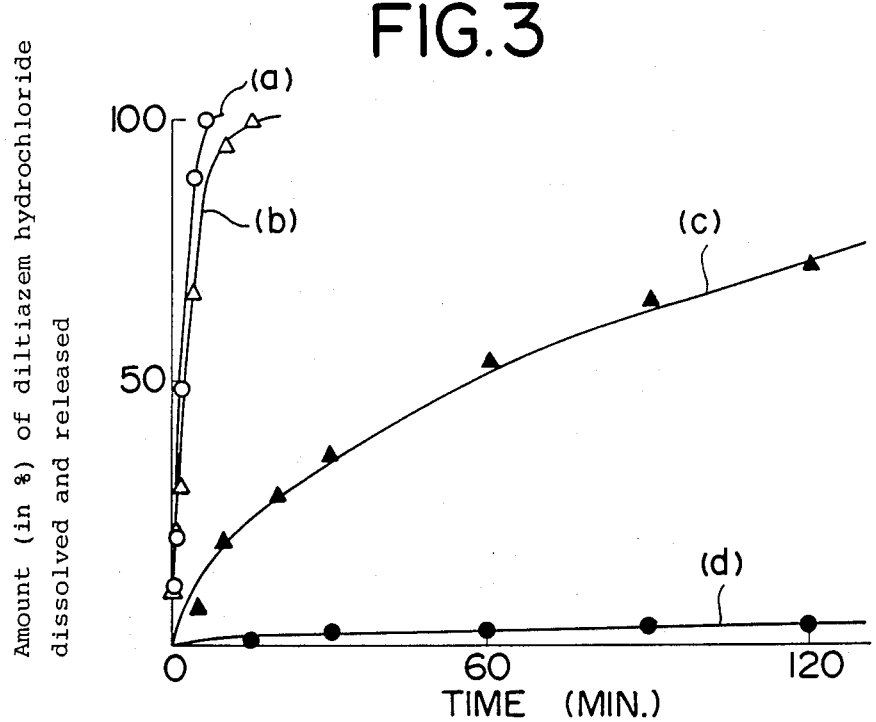
FIGS. 3 and 4 depict the behaviors of dissolution and release of some exemplary inclusion complexes according to this invention, together with those of some exemplary physical mixture, when tested in accordance with the standard test procedure of Japanese Pharmacopoeia.
Figure 4:
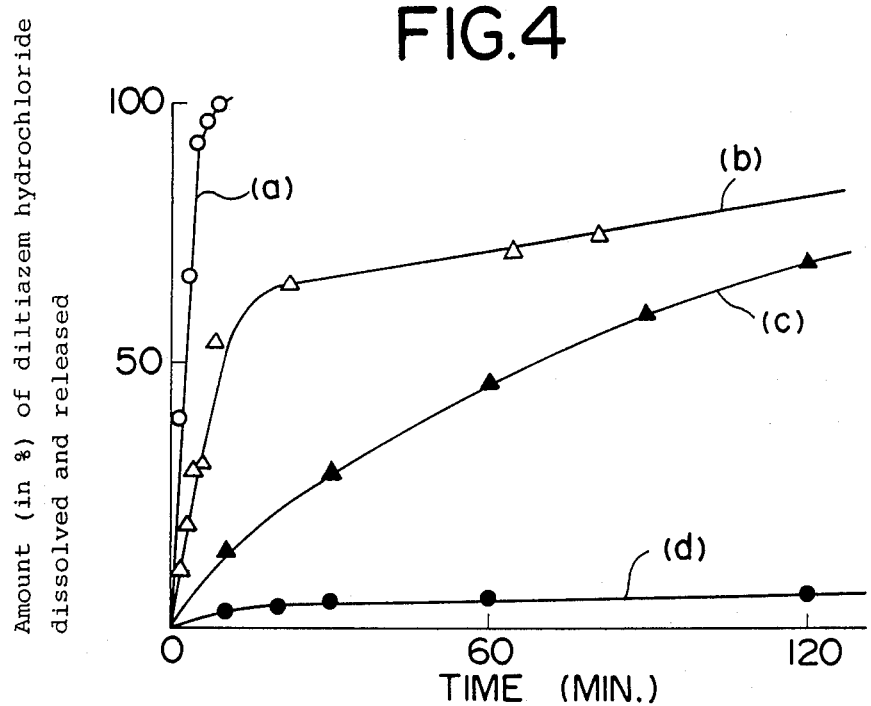
Figure 5:
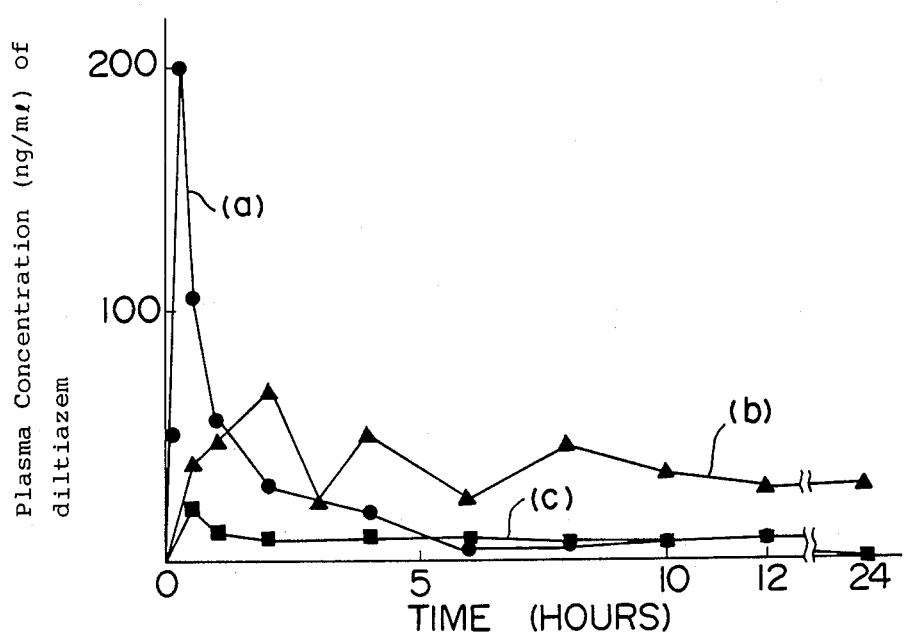

FIG. 5 illustrates the curves of showing variations in the plasma concentration of diltiazem hydrochloride with lapse of time when some exemplary inclusion complexes of diltiazem hydrochloride according to this invention were separately administered to rats in comparison with that for an exemplary physical mixture of diltiazem HCl with starch and FIG. 6 shows the curves of showing variations in the amount (in %) of diltiazem hydrochloride as dissolved and released with lapse of time, when diltiazem hydrochloride was released at controlled rate from some exemplary tablet-shaped mixtures of exemplary inclusion complex of diltiazem HCl with hydrophilic cyclodextrin plus exemplary inclusion complex of diltiazem with hydrophobic ethylated cyclodextrin derivative, while the mixing ratio of the diltiazem HCl-ethylated cyclodextrin complex to the diltiazem HCl-cyclodextrin complex in the mixture was varied.

The inclusion complex of this invention where a medical compound has been complexed with an ethylated cyclodextrin as the guest molecule can show various merits such that it exhibits excellent sustained release property for the medical compound and the release rate can be adjusted without being dependent on pH of the aqueous medium in which the inclusion complex is placed. The inclusion complex of medical compound with a hydrophobic cyclodextrin derivative according to this invention does not require modification upon its formulation into a drug preparation form. In other words, the present invention makes it possible to formulate the inclusion complex as above directly into various drug preparation forms, such as powder, tablets, capsules, other oral preparations, liquid preparations and granules, while said inclusion complex is used without or in association with a conventional, pharmaceutically acceptable vehicle or excipient such as starch, lactose, talc, cellulose powder, CMC and the like.

Production and formulation of certain inclusion complexes in accordance with this invention will be illustrated by the following Examples.

PRODUCTION EXAMPLE 1

In a mortar were placed 1.00 g of diltiazem hydrochloride and 3.39 g of 2,6-DE-$\beta$-CyD, followed by adding a suitable amount of distilled water and mixing the resultant mixture to convert it into a sol-like mixture. The sol-like mixture obtained was kneaded for about 30 minutes, to form the inclusion complex of diltiazem hydrochloride with 2,6-DE-$\beta$-CyD. After drying the mixture containing the resultant inclusion complex under reduced pressure for 3 days, it was screened through a 100-mesh sieve to yield a fine powder of the inclusion complex which was ready for use in Formulation Example 1 below.

FORMULATION EXAMPLE 1

(Tablets)

The inclusion complex as prepared in the Production Example 1 was added with a vehicle, disintegrator, binder and lubricant as specified below. They were then mixed well into an intimate mixture, followed by compression into tablets by a tableting machine.

| | |
|---|---|
| Diltiazem hydrochloride-2,6-DE-$\beta$-CyD inclusion complex (30 mg as the free diltiazem hydrochloride) | 131.7 mg |
| Corn starch | 26.3 mg |
| Calcium carboxymethylcellulose | 30.0 mg |
| Crystalline cellulose | 30.0 mg |
| Magnesium stearate | 2.0 mg |
| Hydroxypropylcellulose | 30.0 mg |
| Total | 250.0 mg |

PRODUCTION EXAMPLE 2

In a mortar were placed 1.00 g of isosorbide nitrate and 6.47 g of 2,6-DE-$\beta$-CyD, followed by adding a suitable amount of distilled water and mixing the resultant mixture to convert it into a sol-like mixture. The sol-like mixture was kneaded for about 30 minutes, to form the inclusion complex of isosorbide nitrate with 2,6-DE-$\beta$-CyD. After drying the mixture containing the resultant inclusion complex under reduced pressure for 3 days, it was screened through a 100-mesh sieve to give a powder of the inclusion complex which was ready for use in Formulation Example 2 below.

FORMULATION EXAMPLE 2

(Granules)

The inclusion complex as prepared in the above Production Example 2 was added with a vehicle, disintegrator and binder as specified below. They were mixed uniformly and formed into granules by a granulating machine. Granules thus obtained were dried and then sifted to provide granules.

| | |
|---|---|
| Isosorbide nitrate-2,6-DE-$\beta$-CyD inclusion complex (10 mg as the free isosorbide nitrate) | 74.7 mg |
| Corn starch | 55.3 mg |
| Lactose | 320.0 mg |
| Hydroxypropylcellulose | 50.0 mg |
| Total | 500.0 mg |

PRODUCTION EXAMPLE 3:

In a mortar were placed 1.00 g of dicardipin hydrochloride and 2.96 g of 2,6-DE-$\beta$-CyD, followed by adding a suitable amount of distilled water and mixing the resultant mixture to convert it into a sol-like mixture. The sol-like mixture was kneaded for about 30 minutes, to form the inclusion complex of dicardipin hydrochloride with 2,6-DE-$\beta$-CyD. After drying the mixture comprising the resultant inclusion complex under reduced pressure for 3 days, it was sifted through a 100-mesh sieve to give a powder of the inclusion complex which was ready for use in Formulation Example 3 below.

FORMULATION EXAMPLE 3

(Capsules)

Polyethylene glycol 400 was heated to 60° C., followed by addition thereto of the inclusion complex of the above Production Example 3, hydroxypropylcellulose, polyethylene glycol 6000, carrageenan and an aqueous solution of pottasium dihydrogenphosphate. The resultant mixture was stirred for 30 minutes to obtain a syrupy mixture. After granulating and drying the syrupy mixture, the resulting granules were filled in hard gelatin capsules.

We claim:

1. A sustained release drug preparation, which comprises an inclusion complex composed of at least one medical compound complexed with at least one hydrophobic alkylated cyclodextrin, as the active ingredient, said medical compound being capable of complexing with said hydrophobic alkylated cyclodextrin to form said inclusion complex.

2. A sustained release pharmaceutical composition in the form of compressed tablets or granules, which comprises (1) a inclusion complex of diltiazem or its acid addition salt, isosorbide or its acid addition salt or dicardipin or its acid addition salt with a hydrophobic alkylated cyclodextrin at a molar ratio of the medical compound to the cyclodextrin derivative of 1:1 to 1:10, plus (ii) an inclusion complex of a medical compound with a hydrophilic cyclodextrin or a hydrophilic cyclodextrin derivative, said medical compound being capable of complexing with a hydrophilic cyclodextrin or a hydrophilic cyclodextrin derivative, at a molar ratio of 1:1 to 1:10, as the active ingredient, and which is in the form of a physical mixture of the inclusion complex (i) with the inclusion complex (ii) at a mixing ratio of 1:2 to 1:0.1 by weight.

3. The sustained release drug preparation as claimed in claim 1, wherein the hydrophobic alkylated cyclodextrin is an ethylated cyclodextrin.

4. The sustained release drug preparation as claimed in claim 3, wherein the ethylated cyclodextrin is heptakis(2,3-di-O-ethyl)-$\beta$-cyclodextrin, heptakis(2,6-di-O-ethyl)-$\beta$-cyclodextrin or heptakis (2,3,6-tri-O-ethyl)-$\beta$-cyclodextrin, or mixtures thereof.

5. The sustained release drug preparation as claimed in claim 1 wherein comprises further a pharmaceutically acceptable carrier for said inclusion complex.

6. The sustained release drug preparation as claimed in claim 1, wherein the hydrophobic alkylated cyclodextin is a mixed methylated/ethylated cyclodextrin.

7. The sustained release drug preparation as claimed in claim 1, further comprising an inclusion complex composed of a medical compound complexed with a hydrophilic naural cyclodextrin or a hydrophilic cyclodextrin derivative.

8. A sustained release drug preparation, which comprises (i) an inclusion complex of a medical compound with a hydrophobic alkylated cyclodextrin, said medical compound being capable of complexing with said hydrophobic alkylated cyclodextrin and (ii) an inclusion complex of a medical compound with a hydrophilic cyclodextrin or a hydrophilic cyclodextrin, said medical compound being capable of complexing with said hydrophilic cyclodextrin or hydrophilic cyclodextrin derivative, as a mixture of the complex (i) with the complex (ii) at a mixing ratio of 1:2 to 1:0.1 by weight, as the active ingredient.

* * * * *